United States Patent [19]

Theis et al.

[11] Patent Number: 5,202,500
[45] Date of Patent: Apr. 13, 1993

[54] PROCESS FOR THE PREPARATION OF ARYLACETALDEHYDE-DIALKYLACETALS

[75] Inventors: Christoph Theis; Wilfried Latz, both of Niederkassel, Fed. Rep. of Germany

[73] Assignee: Huels Aktiengesellschaft, Marl, Fed. Rep. of Germany

[21] Appl. No.: 799,664

[22] Filed: Nov. 21, 1991

Related U.S. Application Data

[63] Continuation of Ser. No. 528,135, May 23, 1990, abandoned.

[30] Foreign Application Priority Data

Jun. 19, 1989 [DE] Fed. Rep. of Germany ....... 3919890

[51] Int. Cl.$^5$ ............................................. C07C 41/50
[52] U.S. Cl. .................................... 568/592; 546/152; 546/339; 548/509; 549/78; 510/56; 510/64
[58] Field of Search ................ 568/592; 546/152, 339; 548/509; 549/78; 510/56, 64

[56] References Cited

FOREIGN PATENT DOCUMENTS

| 174372 | 3/1953 | Austria . |
| 821203 | 11/1951 | Fed. Rep. of Germany . |
| 1077650 | 3/1960 | Fed. Rep. of Germany . |
| 2913677 | 10/1980 | Fed. Rep. of Germany . |
| 1327160 | 4/1963 | France . |
| 2577920 | 8/1986 | France . |

OTHER PUBLICATIONS

De Wolfe, Carboxylic Ortho Acid Derivatives, Academic Press, New York 1970 pp. 272–273.

*Primary Examiner*—Howard T. Mars
*Attorney, Agent, or Firm*—Felfe & Lynch

[57] ABSTRACT

Arylacetaldehyde-dialkylacetals are prepared with high yields and selectivity from the corresponding chloromethylaromatics in the presence of hydrogen chloride acceptors and methyl carbonyl compounds as catalysts and in the presence of orthoesters as water-binding agents by hydroformylation with carbon monoxide and hydrogen.

5 Claims, No Drawings

PROCESS FOR THE PREPARATION OF ARYLACETALDEHYDE-DIALKYLACETALS

This application is a continuation of application Ser. No. 07/528,135, filed May 23, 1990, now abandoned.

FIELD OF THE INVENTION

This invention relates to a novel method for the preparation of arylacetaldehyde-dialkylacetals of the formula:

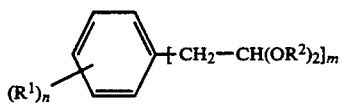

or

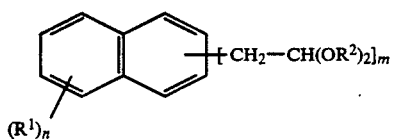

wherein
- $R^1$ is hydrogen, straight or branched alkyl of 1 to 6 carbon atoms, fluorine, chlorine, bromine, iodine, straight or branched alkoxy of 1 to 6 carbon atoms, trifluoromethyl, trichloromethyl, pentafluoroethyl or pentachloroethyl,
- $R^2$ is straight or branched alkyl of 1 to 6 carbon atoms,
- m is an integer from 1 to 3, inclusive, and
- n is an integer from 1 to 5, inclusive, by reacting carbocyclic aromatics or heterocyclic aromatics which are mono- or polysubstituted with halomethyl groups and optionally have one or more groups which are inert under the conditions of the synthesis attached to the aromatic nucleus, with carbon monoxide, hydrogen, orthoesters and alcohols in the presence of a hydrogen halide acceptor and a metal-carbonyl catalyst at elevated pressure and elevated temperature.

BACKGROUND OF THE INVENTION

The preparation of arylacetaldehyde-acetals, especially of dimethyl- and diethylacetals, by the state of the art methods is difficult and expensive.

Phenylacetaldehyde-dimethylacetal or -diethylacetal can be synthesized, for example, by reacting the Grignard compound of benzyl chloride with triethylorthoformate (UK Patent 823,958), by oxidizing cyclooctatetraene with a peracid in methanol (U.S. Pat. No. 2,856,431), by acid-catalytic rearrangement of a 1,2-dimethoxy-cyclooctatetraene (German Auslegeschrift 1 077 650); or by oxidative alcohol addition to styrene in the presence of nobel metal catalysts/alkylnitriles (European Published Application 055 108). Other methods describe the preparation by rearrangement of stryene oxides in the presence of catalysts (European Patent 153,692; Belgian Patent 811 381) with subsequent acetalization of the aldehyde which is formed. Only few methods for preparing substituted arylacetaldehyde-acetals are known. p-Fluorophenylacetaldehyde-diethylacetal is obtained with a moderate yield from the Grignard compound of p-fluorobenzyl-chloride and triethyl orthoformate (French Patent 1 327 160).

According to French Patent 2 577 920, arylacetaldehydeacetals are obtained from halomethyl-substituted aromatics with carbon monoxide and hydrogen in the presence of a basic compound, alcohols and a cobalt-carbonyl catalyst. In order for the reaction to succeed, the presence of an inert organic co-solvent, such as toluene, is essential. This substance ensures that a certain dielectric constant is maintained. During this process, high proportions of a non-distillable residue are formed. In addition to the acetals, large amounts of other substances, especially also the undesired aryl acetates* are formed. With increasing amounts, the reaction is difficult to carry out and already on a 1-mol scale the yields decrease and the specificity is low.

*, i.e. aryl acetic acid esters

OBJECT OF THE INVENTION

It is an object of the present invention to prepare arylacetaldehyde-acetals in a simple and economical manner while
at the same time achieving the highest purity and yields of the end product.

Other objects and advantages of the present invention will become apparent as the description thereof proceeds.

DESCRIPTION OF THE INVENTION

The above object is achieved in accordance with the present invention by the catalytic reaction of halomethyl-aromatics with carbon monoxide, hydrogen and orthoesters in the presence of a basic compound in at least equivalent amounts based on the halomethyl-aromatics. The orthoesters serve as water-binding agents in this reaction. Chloromethyl-aromatics and bromomethylaromatics are preferred as the halomethyl-aromatics.

When monochloromethyl-aromatics and an alkali metal carbonate are used, the reaction of the chloromethyl-aromatics by acetalizing hydroformylization proceeds in accordance with the following formula:

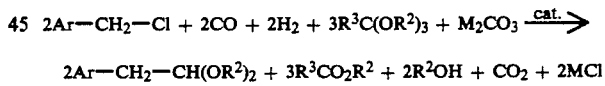

$$2Ar-CH_2-CH(OR^2)_2 + 3R^3CO_2R^2 + 2R^2OH + CO_2 + 2MCl$$

wherein Ar is a carbocyclic or heterocyclic aromatic radical, M is sodium or potassium, $R^2$ is straight or branched alkyl of 1 to 6 carbon atoms, and $R^3$ is hydrogen or $R^2$.

Preferred catalysts are carbonyls of the elements of the 8th subgroup of the periodic system, that is, of cobalt, nickel or iron, the carbonyls of cobalt being preferred. Especially preferred is dicobalt-octacarbonyl of the formula $CO_2(CO)_8$, which is employed in the form of a previously prepared carbonyl, or is formed during or prior to the reaction from cobalt-II compounds, particularly from cobalt-II salts, cobalt-II- oxide or cobalt-II-hydroxide, basic cobalt carbonate or cobalt salts of inorganic or organic acids, such as cobalt bromide, cobalt formate, cobalt acetate, cobalt butyrate, cobalt naphthenate or cobalt stearate, by reaction with carbon monoxide and hydrogen.

The catalysts are employed in amounts of 0.25 to 5 mol-%, preferably 0.5 to 2.0 mol-%, calculated as $CO_2(CO)_8$, based on the halomethyl-aromatics. Under the conditions of the above reaction formula, the mol ratio of carbon monoxide to hydrogen may be in the range of 5:1 to 1:5, preferably in the range 2:1 to 1:2, and especially preferably 1:1 with up to 20% tolerance. The total pressure during the reaction may range between 5 and 30 MPa, preferably between 5 and 25 MPa, and especially preferably between 10 and 25 MPa. The reaction temperature should be between 90° and 130° C., preferably between 95° and 110° C. In practice, the heterogeneous reaction mixture which is contained in the autoclave under the described carbon monoxide/hydrogen pressures is heated until there is a visible drop in pressure due to consumption of carbon monoxide and hydrogen. The resulting reaction temperature is maintained during the entire reaction.

The amount of basic compound to be used is at least an equivalent amount, preferably 1 to 1.25 equivalents of the hydrogen chloride which is formed. Suitable basic compounds are, among others, carbonates, bicarbonates, hydrogen phosphates, and possibly also hydroxides of sodium and potassium. An excess of the basic compound is not critical, but stoichiometric amounts are preferably used. Preferred are alkali metal carbonates and alkali metal bicarbonates, especially sodium carbonate and sodium bicarbonate. When alkali metal carbonates are used as a hydrogen chloride acceptor, 1.5 mols of orthoester must be used, and when alkali metal bicarbonates are used, 2.0 mols of orthoester must be used per mol of reacted chloromethyl group pursuant to the reaction equation. The orthoesters must be used in at least equivalent amounts, pursuant to the reaction equation. An excess of up to 50 mol-% of orthoester is possible and improves the yield. The use of orthoesters as acetalizing and water-binding agents in this carbonylation reaction is new and for several reasons surprising. According to P. Piacenti and M. Bianchi, Organic Synthesis via Metal Carbonyls, Vol. II, page 28 ff. (Editors: I. Wender and P. Pino, published by Willey & Sons, New York 1977), orthoesters are rapidly hydroformylated and simultaneously acetalized with high yields under the influence of carbon monoxide and hydrogen (1:1) in the presence of dicobalt octacarbonyl and optionally alcohols at pressures above 8 MPa and temperatures above 80° C. Under approximately the same conditions as those of the present process, this reaction with carbon monoxide and hydrogen surprisingly does not occur unless large excess amounts of orthoesters are present. Among the orthoesters (orthocarboxylic acid trialkyl esters) as defined herein, the dimethyl orthoformate and ethyl orthoformate are preferred. Moreover, it could not have that the acidity of the reaction medium is sufficient in the presence of the basic compounds to ensure a practically quantitative acetalization of the aldehydes produced in situ. On the other hand, despite the heterogeneity of the reaction mixture, the acidity is not so high that it negatively affects the effectiveness of the catalyst. The addition of small amounts of alcohols improves the acetal yield and facilitates the performance of the reaction. Preferably the same alcohol is added as is formed from the particular orthoester which is employed. The ratio of chloromethyl aromatics to alcohol should be from 5:1 to 1:5 mols. Surprisingly, aryl acetates which are formed from benzyl chlorides in the absence of orthoesters are not formed.

The starting materials are especially halomethyl-aryls of the formula

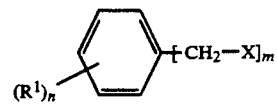

or

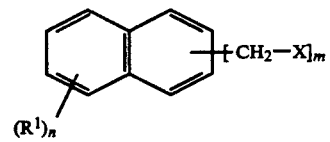

wherein 1 to 2 carbon atoms in the aryl moiety may be replaced by a nitrogen, oxygen or sulfur atom, X is fluorine, chlorine, bromine or iodine, R$^1$ is hydrogen, R$^2$, fluorine, chlorine, bromine, iodine, alkoxy with straight or branched alkyl moieties of 1 to 6 carbon atoms, trifluoromethyl, trichloromethyl, pentafluoroethyl, pentachloroethyl, carboxymethoxy, carboxy-ethoxy, hydroxy or nitro, R$^2$ is straight or branched alkyl of 1 to 6 carbon atoms, n is an integer from 1 to 5, inclusive, and m is an integer from 1 to 3, inclusive, and the sum of m+n is no more than 6 in the case of formula I, and no more than 8 in the case of formula II. Preferred are mono-halomethyl-aromatics wherein m is 1, and secondarily di-halomethyl-aromatics wherein m is 2, and in which the number of substituents R$^1$ is preferably 1, 2 or 3. The number of substituents R$^1$ is most preferably 1. The aryl radicals are the carbocyclic moieties phenyl or naphthyl, but also heteroaryls such as thienyl, pyridyl, quinolyl or indole radicals, as well as other mono- and polycyclic substituted or unsubstituted aryl radicals. Aryl radicals with 1 or 2 rings consisting solely of carbon atoms are preferred. In the starting materials the aryl radical and the substituent R$^1$ correspond to the process products.

The process according to the present invention has the advantage that it is a simple and safe performance of the reaction with a high specificity, that is, that it forms only minor amounts of side products and produces high yields of the desired products.

The reaction mixture can be worked up, optionally after removal of the alkali metal halide and addition of water, by destruction of the carbonyl catalyst with the aid of hydrogen peroxide in the form of an aqueous solution at a pH between 4 and 5. The suspension divides into an aqueous phase and an organic phase. Thereafter, the low boiling point components, that is, the substances having a lower boiling point than the boiling point of the reaction product, are removed. After admixture with minor amounts of an alkali metal hydroxide or an aqueous solution thereof, the reaction product is recovered by subsequent vacuum distillation and possibly subsequent rectification.

The following examples illustrate the present invention and will enable others skilled in the art to understand it more completely. It should be understood, however, that the invention is not limited solely to the particular examples given below.

EXAMPLE 1

189.8 g of benzyl chloride (1.5 mols), 318.0 g of trimethyl orthoformate (3.0 mols), 32.0 g of methanol (1.0 mol), 80.0 g of sodium carbonate (0.75 mol) and 7.5 g of CO$_2$(CO)$_8$ (1.46 mol-% based on the benzyl chloride) were introduced into a 1-liter autoclave.

After rinsing with carbon monoxide, 10 MPa of hydrogen and 10 MPa of carbon monoxide were introduced, and the reactor was heated. The reaction commenced at an internal temperature of 100° C., and the consumed gases were replaced at a ratio of 1:1 in the pressure range of 22 to 24 MPa corresponding to the progress of the reaction; after 1 hour the gas uptake was complete, and after a post-reaction period of 1 hour, the reactor was cooled and the pressure was released.

The suspension withdrawn from the reactor was worked up as follows: According to the gas chromatogram of the liquid phase, the benzyl chloride reacted practically quantitatively. The water content was less than 0.25%. The suspension was admixed with 350 ml of water, and the two-phase system formed thereby was admixed with 15 ml of 30 wt.-% aqueous hydrogen peroxide at a pH of 4.5 while thoroughly stirring, and the mixture was then refluxed for 1 hours. After cooling, the organic phase was separated, washed with 50 ml of 5 wt.-% sodium hydroxide and distilled under normal pressure. After distilling off the low boiling point components, 4.5 g of 50 wt.-% sodium hydroxide were added at a sump temperature of 120° C., the mixture was stirred at this temperature for 10 minutes, and the cooled sump was then subjected to vacuum distillation.

206.9 g of distillate (bp=87 to 91° C. at 10 hPa) were obtained. 16.9 g of distillation residue remained behind. The gas chromatogram of this raw product contained 95.4 liquid-% phenylacetaldehyde-dimethylacetal in addition to 3.2 liquid-% of 2-phenylethanol; this corresponds to an acetal yield of 79.3%, based on the benzyl chloride which was used. The raw product was worked up by rectification to yield a product with a purity of more than 99.5%.

Comparative example (according to French Patent 2 577 920, example 13)

75.9 g of benzyl chloride (0.6 mol), 227.4 g of ethanol (4.94 mols), 192 ml of toluene, 31.9 g of sodium carbonate (0.3 mol) and 7.0 g of CO$_2$(CO)$_8$ (3.4 mol-% based on the benzyl chloride) were introduced into a 1-liter autoclave. The autoclave was closed, rinsed with carbon monoxide, and after introducing 2.5 MPa of hydrogen and 2.5 MPa of carbon monoxide the internal temperature was raised to 80° C. When the gas uptake began, carbon monoxide and hydrogen in a ratio of 1:1 were replaced at the uptake rate within a pressure range of 5 to 6 MPa until the gas uptake ceased. After cooling the reactor and releasing the pressure, the reaction solution was worked up as described in Example 1.

52.3 g of raw product were obtained by distillation, and 34.8 g of non-distillable substances remained behind as a residue. Gaschromatographic analysis of the raw product showed that it contained 5.2 liquid-% benzyl chloride, 0.4 liquid-% phenylacetaldehyde, 0.2 liquid-% 2-phenylethanol, 12.0 liquid-% ethyl phenylacetate as well as 78.8 liquid-% phenylacetaldehydediethylacetal. Based on this analysis, the yield of phenylacetaldehydediacetal was 37.3% of theory. 94.8% of the benzyl chloride had reacted.

EXAMPLE 2

Example 1 was repeated, but 1.5 mols of sodium bicarbonate were used instead of sodium carbonate. Gaschromatographic analysis of the raw product showed that the yield of phenylacetaldehyde-dimethylacetal was 77.7% of theory.

EXAMPLE 3

Example 1 was repeated, except that 0.75 mol of potassium carbonate was used instead of sodium carbonate. The yield of phenylacetaldehyde-dimethylacetal was 60.2% of theory.

EXAMPLE 4

Example 1 was repeated, except that 1.5 mols of potassium bicarbonate were used. The yield of phenylacetaldehydedimethylacetal was 74.9% of theory.

The reaction and the recovery of the reaction product in Examples 5 to 22 as shown in the following Table 1 were performed in analogy to Example 1.

TABLE 1

| Example | Mol Orthoester | Mol Methanol | Base [Mol] | Reaction Pressure [MPa] | CO:H$_2$ | Acetal Yield [%] |
|---|---|---|---|---|---|---|
| 5  | 2.81  | 1.0   | Na$_2$CO$_3$ [0.75] | 22–24     | 2:1 | 58.8 |
| 6  | 2.81  | 1.0   | Na$_2$CO$_3$ [0.75] | 22–24     | 1:2 | 71.3 |
| 7  | 2.81  | 1.0   | NaHCO$_3$ [1.5]     | 22–24     | 2:1 | 56.0 |
| 8  | 2.81  | 1.0   | NaHCO$_3$ [1.5]     | 22–24     | 1:2 | 61.4 |
| 9  | 2.81  | 1.0   | Na$_2$CO$_3$ [0.75] | 5–7       | 1:1 | 57.1 |
| 10 | 2.81  | 1.0   | Na$_2$CO$_3$ [0.75] | 9–11      | 1:1 | 74.0 |
| 11 | 2.81  | 1.0   | Na$_2$CO$_3$ [0.75] | 13–15     | 1:1 | 78.8 |
| 12 | 2.81  | 1.0   | Na$_2$CO$_3$ [0.75] | 16.5–18.5 | 1:1 | 79.7 |
| 13 | 2.81  | 1.0   | Na$_2$CO$_3$ [0.75] | 19–21     | 1:1 | 81.2 |
| 14 | 2.81  | 1.0   | Na$_2$CO$_3$ [0.75] | 23–25     | 1:1 | 79.5 |
| 15 | 2.81  | 0     | Na$_2$CO$_3$ [0.75] | 13–15     | 1:1 | 72.9 |
| 16 | 2.81  | 0.75  | Na$_2$CO$_3$ [0.75] | 13–15     | 1:1 | 77.4 |
| 17 | 2.81  | 1.125 | Na$_2$CO$_3$ [0.75] | 13–15     | 1:1 | 79.4 |
| 18 | 2.81  | 1.5   | Na$_2$CO$_3$ [0.75] | 13–15     | 1:1 | 76.8 |
| 19 | 2.0   | 1.0   | Na$_2$CO$_3$ [0.75] | 13–15     | 1:1 | 72.4 |
| 20 | 2.25  | 1.0   | Na$_2$CO$_3$ [0.75] | 13–15     | 1:1 | 78.5 |
| 21 | 2.40  | 1.125 | Na$_2$CO$_3$ [0.75] | 13–15     | 1:1 | 80.0 |
| 22 | 2.625 | 1.125 | Na$_2$CO$_3$ [0.75] | 13–15     | 1:1 | 76.8 |

EXAMPLE 23

1.5 mols of benzyl chloride, 1.5 mols of ethanol, 2.81 mols of triethyl orthoformate and 0.75 mol of sodium carbonate were reacted in analogy to Example 1, and the reaction mixture was worked up as there described. The resulting raw product had a boiling point of 94° to 104° C. (10 hPa), and gas chromatographic analysis of its composition showed that the yield of phenylacetaldehyde-diacetal was 72.8% of theory.

EXAMPLE 24

In analogy to Example 23, the starting compounds mentioned therein were reacted in the manner described, except that sodium carbonate was replaced by 1.5 mols of sodium bicarbonate. After working up the reaction mixture as described in Example 1, a raw distillate was obtained, the composition of which indicated that the yield of phenylacetaldehyde-diethylacetal was 63.3% of theory.

Examples 25 to 38 shown in the following Table 2 were performed in analogy to Example 1, by using substituted chloromethyl-aromatics, stoichiometric amounts of sodium carbonate and with double molar concentration of trimethyl orthoformate per reactive chloromethyl group; the other reaction-specific parameters are shown in this Table as well. Degree of reaction and water content corresponded to the preceding Examples. After working up the reaction mixture in analogy to Example 1, the very pure raw products produced the yields shown in Table 2, based on amount of chloromethyl-aromatic starting compounds. All of the products exhibited the correct spectroscopic data corresponding to their constitution.

peroxide. The separated organic phase was worked up by distillation in analogy to Example 1 by using 7.5 g of 50 wt.-% sodium hydroxide. Upon vacuum distillation of the sump, 454 g of raw product with an acetal content of 94 liquid-% were obtained. The yield of p-chloromethylphenyl-acetaldehydedimethyl acetal was 79.2% of theory.

EXAMPLE 41

Example 40 was repeated, but 477.0 g (4.5 mols) of trimethyl orthoformate were used. After working up the reaction suspension and distilling the sump as described in Example 40, 439.3 g of raw product with an acetal content of 92.6 liquid-% were obtained. The yield of p-methylphenyl-acetaldehydedimethylacetal was 75.4% of theory.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

TABLE 2

| Example | Starting Compound | [mol] | Mol Methanol | $Co_2(CO)_3$ Concen. [Mol-%] | Reaction-Pressure [MPa] | Arylacetaldehyde-dimethylacetal Boiling point [°C./hPa] | Yield [%] |
|---|---|---|---|---|---|---|---|
| 25 | m-Methoxy-benzylchloride | [0.64] | 0.48 | 1.46 | 19–21 | 125–31/10 | 72.7 |
| 26 | o-Methyl-benzylchloride | [1.50] | 1.125 | 1.46 | 16.5–18.5 | 95–103/10 | 75.0 |
| 27 | m-Methyl-benzylchloride | [1.50] | 1.05 | 1.46 | 16.5–18.6 | 96–102/10 | 76.3 |
| 28 | p-Methyl-benzylchloride | [1.50] | 1.125 | 1.46 | 23–25 | 94–102/10 | 79.5 |
| 29 | p-Methyl-benzylchloride | [1.50] | 1.125 | 0.50 | 16.5–18.5 | 94–102/10 | 74.1 |
| 30 | o-Chloro-benzylchloride | [1.50] | 1.125 | 1.46 | 16.5–18.5 | 102–108/10 | 78.8 |
| 31 | m-chloro-benzylchloride | [0.674] | 0.50 | 1.34 | 16.5–18.5 | 115–118/10 | 72.9 |
| 32 | p-Chloro-benzylchloride | [1.0] | 4.00 | 1.46 | 16.5–18.5 | 116–120/10 | 48.4 |
| 33 | p-Chloro-benzylchloride | [1.50] | 2.81 | 1.46 | 16.5–18.5 | 116–120/10 | 59.7 |
| 34 | p-Fluoro-benzylchloride | [1.00] | 2.50 | 1.46 | 16.5–18.5 | 89–94/10 | 74.1 |
| 35 | p-Fluoro-benzylchloride | [0.675] | 0.50 | 1.34 | 16.5–18.5 | 89–94/10 | 67.9 |
| 36 | m-Trifluoromethyl-benzylchloride | [0.51] | 0.38 | 1.49 | 20 | 79–87/10 | 65.8 |
| 37 | m-Methoxycarbonyl-benzylchloride | [1.50] | 1.125 | 1.46 | 16.5–18.5 | 121–122/1.5 | 49.4 |
| 38 | 1-Chloromethyl-napthaline | [1.50] | 1.125 | 1.46 | 16.5–18.5 | 139–142/4.0 | 51.0 |

EXAMPLE 39

In analogy to Example 1 0.75 mol of p-chloromethyl-benzylchloride, 2.0 mols of trimethyl orthoformate, 1.125 mols of methanol, 0.75 mol of sodium carbonate and 7.5 g of $CO_2(CO)_8$ were reacted at a temperature of 106° to 108° C. at a pressure of 16.5 to 18.5 MPa. After working up the reaction mixture as described in Example 1, a raw product having a boiling point of 126° to 128° C. (1.0 hPa) was obtained, the composition of which showed that the yield of 4-(2'2'-dimethoxyethyl-phenyl)-acetaldehydedimethylacetal was 34.2% of theory.

EXAMPLE 40

421.4 g (3.0 mols) of p-chloromethyl-benzylchloride, 596.3 g (5.625 mols) of trimethyl orthoformate, 72.0 g (2.25 mols) of methanol, 160.0 g (1.5 mols) of sodium bicarbonate and 10.3 g of $CO_2(CO)_8$ (1.0 mol-%) based on the amount of p-chloromethylbenzylchloride) were introduced into a 2-liter autoclave. After rinsing the autoclave with carbon monoxide, hydrogen and carbon monoxide in a ratio of 1:1 were introduced under pressure, and the reaction was carried out at 102° C. and a reaction pressure of 16.5 to 18.5 MPa. The reaction suspension was worked up in analogy to Example 1 by using 700 ml of water and 20 ml of 30 wt.-% hydrogen 1. In a process for the preparation of an aryl acetaldehyde-dialkylacetal of the formula

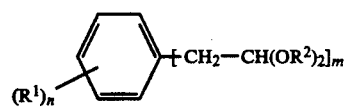

or

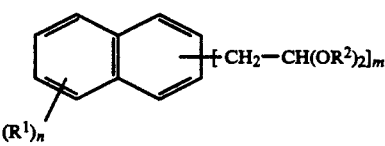

wherein $R^1$ is hydrogen, straight or branched alkyl of 1 to 6 carbon atoms, fluorine, chlorine, bromine, iodine, straight or branched alkoxy of 1 to 6 carbon atoms, trifluoromethyl, trichloromethyl, pentafluoroethyl or pentachloroethyl, $R^2$ is straight or branched alkyl of 1 to 6 carbon atoms, m is an integer from 1 to 3, inclusive, and n is an integer from 1 to 5, inclusive,
by reacting a halomethyl-aromatic compound of the formula

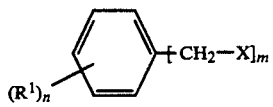   I or

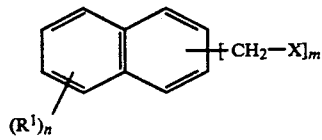   II wherein
$R^1$, n and m have the meanings previously defined, and
X is chlorine, bromine or iodine, in the presence of a carbonyl compound of a metal of the 8th subgroup of the periodic system as a catalyst, with at least equivalent amounts of carbon monoxide and hydrogen at elevated pressure and elevated temperature and in the presence of at least one equivalent of a basic compound as a hydrogen halide acceptor, the improvement which comprises performing the reaction in the presence of an orthoester of the formula $$R^3\text{—}C(OR^2)_3$$

wherein
$R^2$ has the meanings previously defined, and
$R^3$ is hydrogen or straight or branched alkyl of 1 to 6 carbon atoms, and recovering the reaction product.

2. The process of claim 1, which is performed additionally in the presence of an alcohol of the formula $R^2$OH, wherein $R^2$ is straight or branched alkyl of 1 to 6 carbon atoms.

3. The process of claim 2, wherein said alcohol is identical to the alcohol formed by the reaction.

4. The process of claim 1, wherein said orthoester is methyl orthoformate or ethyl orthoformate.

5. The process of claim 1, wherein the recovery of the reaction product is effected by destroying the catalyst with aqueous hydrogen peroxide, removal of the low boiling point components by distillation, addition of an alkali metal hydroxide, and vacuum distillation.

* * * * *